United States Patent [19]

Kameswaran

[11] Patent Number: 5,446,170
[45] Date of Patent: Aug. 29, 1995

[54] PROCESS FOR THE MANUFACTURE OF INSECTICIDAL ARYLPYRROLES VIA OXAZOLE AMINE INTERMEDIATES

[75] Inventor: Venkataraman Kameswaran, Princeton Junction, N.J.

[73] Assignee: American Cyanamid Company, Wayne, N.J.

[21] Appl. No.: 343,147

[22] Filed: Nov. 22, 1994

[51] Int. Cl.$^6$ .................. C07D 207/30; C07D 405/02; C07D 409/02
[52] U.S. Cl. ..................................... 548/517; 548/525; 548/526; 548/527; 548/560; 548/561
[58] Field of Search ............... 548/517, 525, 526, 527, 548/560, 561

[56] References Cited

U.S. PATENT DOCUMENTS

| | | | |
|---|---|---|---|
| 5,030,735 | 7/1991 | Addor et al. | 548/531 |
| 5,130,328 | 7/1992 | Kameswaran | 514/426 |
| 5,145,986 | 9/1992 | Kameswaran et al. | 548/531 |
| 5,286,743 | 2/1994 | Kuhn et al. | 514/424 |
| 5,288,901 | 2/1994 | Doehner et al. | 562/449 |

OTHER PUBLICATIONS

CA117:150881m Preparation . . . said agents. Doehner, p. 815, 1992.
CA119:8679z Preparation . . . pesticides. Ehrenfreund et al., p. 892, 1993.
J. Org. Chem., 45, 1301–1308, Synthetic . . . Compounds, McEwen et al., 1980.
Deyrup, J. A. and Killion, K. K., Journal of Heterocyclic Chemistry, 9 (5) 1045–48 (1972).
Poupert, J.; Bruylants, A.; Crooy, P., Synthesis (11), 622–4 (1972).
Tanaka, C. and Haruko, A., Yakugaku Zasshi, 92 (4), 436–43 (Abstract), 1971.
McEwen, W. E., Grossi, A. V.; MacDonald, R. J.; Stamegna, A. P., Journal of Organic Chemistry, 1980, 45, 1301–1308.
Jones, R. A., *Pyrroles Part One*, J. Wiley and Sons (1990), p. 167–170.

*Primary Examiner*—Joseph K. McKane

[57] ABSTRACT

The present invention provides a process for the manufacture of 2-aryl-5-(perfluoroalkyl)pyrrole-3-carbonitrile comprising the cycloaddition of 5-amino-4-aryl-2-perfluoroalkyl-1,3-oxazole and the appropriate 1,3-dipolarifile. The arylpyrrole-3-carbonitrile product and its derivatives are highly effective insecticidal, acaricidal and nematocidal agents.

9 Claims, No Drawings

PROCESS FOR THE MANUFACTURE OF INSECTICIDAL ARYLPYRROLES VIA OXAZOLE AMINE INTERMEDIATES

BACKGROUND OF THE INVENTION

Arylpyrrole carbonitrile compounds are highly effective insecticidal, acaricidal and nematocidal agents with a unique mode of action and a broad spectrum of activity. In particular, 2-aryl-5-(trifluoromethyl)pyrrole-3-carbonitrile compounds demonstrate effective control across a wide array of pests and can control resistant pests such as pyrethroid-, organophosphate-, cyclodiene-, organochlorine-, organotin-, carbamate-, and benzophenylurea-resistant biotypes of *Helicoverpa/Heliothis spp.*, *Spodoptera spp.*, *Trichoplusia spp.*, *Pseudoplusia spp.* and *Tetranychus spp.*. Because there is no apparent cross-resistance, 2-aryl-5-trifluoromethylpyrrole-3-carbonitrile compounds and their derivatives have potential for use in resistance management programs. Further, said pyrroles have little effect on beneficial species making them excellent candidates for integrated pest management programs, as well. These programs are essential in today's crop production.

Therefore, methods to prepare said pyrroles and intermediates to facilitate their manufacture are of great value. Among the methods known to prepare 2-aryl-5-(trifluoromethyl)pyrrole-3-carbonitrile is the 1,3-dipolar cycloaddition of the mesoionic intermediate product of the acid catalyzed cyclization of a Reissert compound with a suitable alkyne to give an N-substituted pyrrole product as described by W. M. McEwen, et al, Journal of Organic Chemistry, 1980, 45, 1301–1308. Similarly, munchnones (which are also zwitterionic intermediates) undergo 1,3-dipolar cycloaddition to give N-substituted pyrroles. In addition, on a manufacturing scale, the 1,3-dipolar cycloaddition of 3-oxazolin-5-one with 2-chloroacrylonitrile is described in U.S. Pat. No. 5,030,735.

It is an object of this invention to provide an alternate source of important intermediate compounds and manufacturing routes to a new class of highly effective pesticidal compounds.

It is a feature of this invention that the process of manufacture provides a regiospecific product.

It is an advantage of this invention that the process of manufacture provides an N-unsubstituted pyrrole (NH-pyrrole) intermediate which is capable of further derivatization of the pyrrole ring nitrogen to give a wide variety of pesticidally active pyrrole products.

SUMMARY OF THE INVENTION

The present invention provides a process for the manufacture of an arylpyrrole compound of formula IV

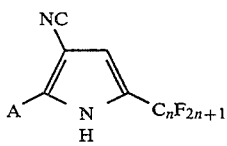

(IV)

wherein n is an integer of 1, 2, 3, 4, 5, 6, 7 or 8; A is

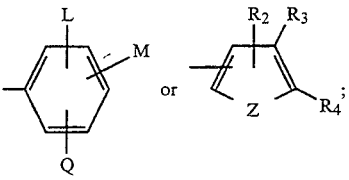

L is hydrogen or halogen;
M and Q are each independently hydrogen, halogen CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl or when M and Q are on adjacent positions they may be taken together with the carbon atoms to which they are attached to form a ring in which MQ represents the structure

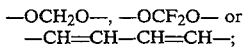

$R_2$, $R_3$ and $R_4$ are each independently hydrogen, halogen, $NO_2$, CHO or $R_3$ and $R_4$ may be taken together with the atoms to which they are attached to form a ring in which $R_3R_4$ is represented by the structure

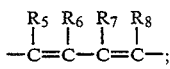

$R_5$, $R_6$, $R_7$ and $R_8$ are each independently hydrogen, halogen, CN or $NO_2$; and
Z is O or S which comprises reacting an oxazole amine intermediate of formula I or tautomer thereof

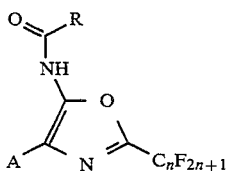

(I)

wherein n and A are described above and
R is $C_1$-$C_6$alkyl, $C_1$-$C_6$haloalkyl, $COOR_1$, or phenyl optionally substituted with one or more halogen, $NO_2$, CN, $C_1$-$C_4$alkoxy, $C_1$-$C_4$alkylthio, $C_1$-$C_4$alkyl or $C_1$-$C_4$haloalkyl groups and
$R_1$ is $C_1$-$C_4$alkyl or $C_1$-$C_4$haloalkyl with at least one molar equivalent of 2-haloacrylonitrile or 2,3-dihalopropionitrile in the presence of a base and optionally in the presence of a solvent.

Also provided are oxazole amine intermediates of formula I and a method for their preparation.

DETAILED DESCRIPTION OF THE INVENTION

Processes, to be useful on a manufacturing scale, preferentially contain key intermediate compounds which may be obtained in high to quantitative yield, which are stable either upon isolation or in situ, which may be produced from simple or readily available starting materials and which may be readily converted to the desired end-product of manufacture in a minimum of reaction steps, in optimum yield and purity and, if applicable, regio-or stereospecifically.

It has now been found that 5-amino-4-aryl-2-perfluoroalkyl-1,3-oxazole derivatives of formula I and tautomers thereof are effective key intermediates in the manufacture of 2-aryl-5-(perfluoroalkyl)pyrrole-3-carbonitrile insecticidal, acaricidal and nematocidal compounds. The oxazole amine derivatives of the present invention have the structure of formula I

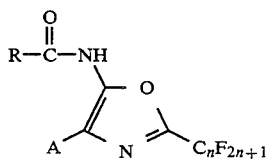

wherein n is an integer of 1, 2, 3, 4, 5, 6, 7 or 8;

R is $C_1$-$C_6$alkyl, $C_1$-$C_6$haloalkyl, $COOR_1$, or phenyl optionally substituted with one or more halogen, $NO_2$, CN, $C_1$-$C_4$alkoxy, $C_1$-$C_4$alkylthio, $C_1$-$C_4$alkyl or $C_1$-$C_4$haloalkyl groups;

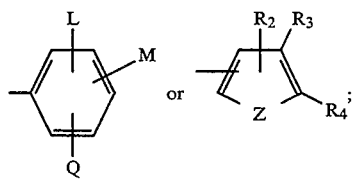

L is hydrogen or halogen;

M and Q are each independently hydrogen, halogen CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl or when M and Q are on adjacent positions they may be taken together with the carbon atoms to which they are attached to form a ring in which MQ represents the structure —OCH₂O—, —OCF₂O— or
—CH=CH—CH=CH—;

$R_2$, $R_3$ and $R_4$ are each independently hydrogen, halogen, $NO_2$, CHO or $R_3$ and $R_4$ may be taken together with the atoms to which they are attached to form a ring in which $R_3R_4$ is represented by the structure

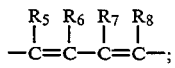

$R_5$, $R_6$, $R_7$ and $R_8$ are each independently hydrogen, halogen, CN or $NO_2$; and Z is O or S.

The 5-amino-4-aryl-2-perfluoroalkyl-1,3-oxazole derivatives of formula I may be represented by their tautomeric 5-imino-4-aryl-2-perfluoroalkyl-3-oxazoline (formula Ia) or 5-imino-4-aryl-2-perfluoroalkyl-2-oxazoline (formula Ib) structures shown below wherein R, A and n are as described above.

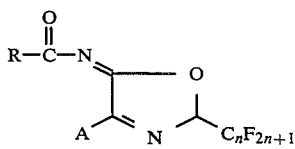

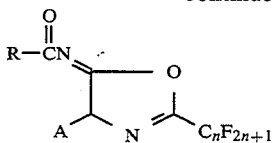

The term halogen designates Cl, Br, F, or I and the term haloalkyl encompasses any alkyl group with n carbon atoms which contains from one to 2n+1 halogen atoms.

Intermediates of formula I and their tautomers are readily prepared by cyclizing perfluoroalkanoyl aminonitrile compounds of formula II

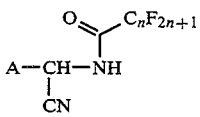

wherein A is as defined hereinabove in the presence of an acid and an acyl halide of formula III

wherein X is Cl or Br and R is as defined hereinabove, optionally in the presence of a solvent. The reaction is shown in flow diagram I Flow Diagram I

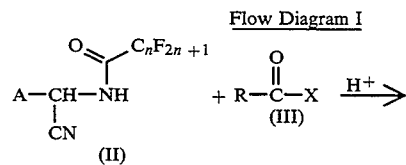

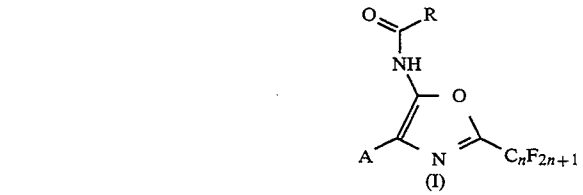

Compounds of formula II and their preparation are described in co-pending patent application Ser. No. 08/175,845 filed Dec. 30, 1993 and incorporated herein by reference thereto.

Among the solvents suitable for use in the preparation of the formula I intermediate are aromatic hydrocarbons and halogenated aromatic hydrocarbons, preferably aromatic hydrocarbons such as toluene, benzene, xylene, and the like, more preferably toluene or xylene or combinations thereof.

Acids suitable for use in the cyclization include sulfuric acid, methanesulfonic acid, benzenesulfonic acid, p-toluenesulfonic acid, fluoroboric acid, boron trifluoride complexes and the like. Boron trifluoride complexes may include $BF_3$ etherate, $BF_3$ methanol complex, $BF_3$ ethanol complex and the like.

Surprisingly, it has been found that the formula I oxazole amine intermediate undergoes a 1,3-dipolar cycloaddition with 2-haloacrylonitrile or 2,3-dihalopropionitrile in the presence of a base and optionally in the presence of a solvent to regiospecifically give 2-aryl-5- perfluoroalkylpyrrole-3-carbonitrile compounds of formula IV in a simple one step conversion. The reaction, using 2-haloacrylonitrile as the 1,3-dipolarifile, is shown in flow diagram II wherein X is Cl or Br.

Flow Diagram II

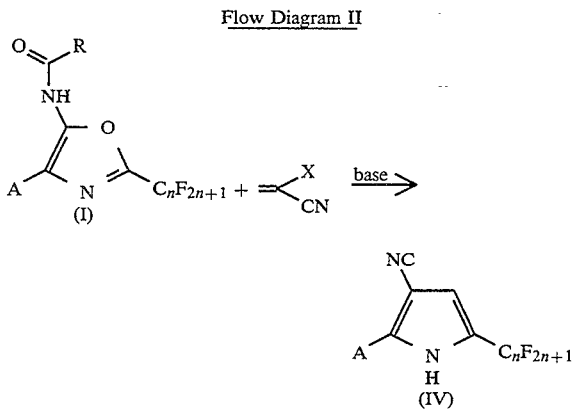

Among the bases which may be used in the inventive process are alkali metal carbonates or bicarbonates, tri($C_1$-$C_4$alkyl)amines, alkali metal hydroxides, alkali metal acetates, 4-dimethylaminopyridine, pyridine, and the like. Preferred bases are alkali metal carbonates and tri($C_1$-$C_4$alkyl)amines such as triethylamine.

Solvents contemplated for use in the process of the invention are those organic solvents which are commonly suitable for manufacturing processes and in which the reactants are soluble such as acetonitrile, toluene, xylene, dimethyl formamide and the like or combinations thereof.

In accordance with the process of the invention a perfluoroalkanoyl aminonitrile of formula II is admixed with approximately an equimolar amount of an acylhalide of formula III in the presence of an acid, optionally in the presence of a solvent to form the formula I oxazole amine intermediate. Said intermediate may be isolated using conventional techniques such as filtration or extraction. The rate of formation of the formula I oxazole may be increased with increased temperature. However, it is understood that excessively high reaction temperatures will cause decomposition and a decrease in product yield and purity. Typical reaction temperatures may range from 20°–100° C., preferably 60°–90° C. The isolated oxazole amine intermediate may then be converted to the desired formula IV arylpyrrole product by admixing said oxazole with about one molar equivalent of 2-haloacrylonitrile or 2,3-dihalopropionitrile in the presence of at least one molar equivalent of a base and optionally in the presence of a solvent.

Alternatively, the formula I oxazole amine intermediate may be formed in situ and, without isolation, converted directly to the desired formula IV arylpyrrole product with retention of regiospecificity. In this embodiment of the invention (shown in Flow Diagram III), the perfluoroalkanoyl aminonitrile of formula II is admixed with about one molar equivalent of an acylhalide of formula III in the presence of an acid and optionally in the presence of a solvent. When the formation of the formula I oxazole amine is complete, the reaction mixture is treated with at least one molar equivalent of 2-haloacrylonitrile, or 2,3-dihalopropionitrile, and at least one molar equivalent of a base. The formula IV arylpyrrole product may be isolated by conventional methods such as dilution of the reaction mixture with water followed by filtration or extraction.

Flow Diagram III

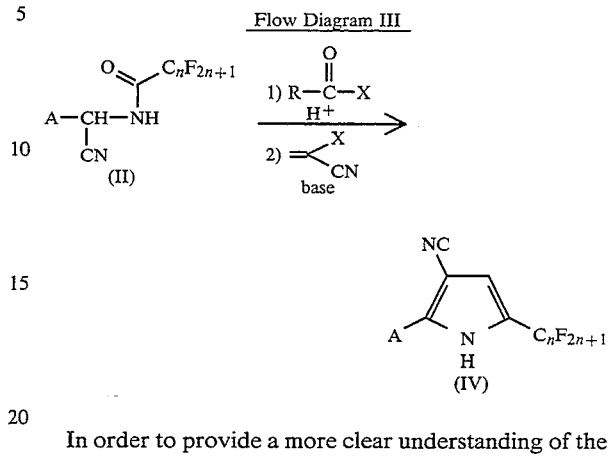

In order to provide a more clear understanding of the invention, the following examples are set forth below. These examples are merely illustrative and are not to be understood to limit the scope or underlying principles of the invention in any way.

The terms $^1$HNMR, $^{13}$CNMR and $^{19}$FNMR designate proton, carbon 13 and fluorine 19 nuclear magnetic resonance, respectively. The term HPLC designates high performance liquid chromatography and GLC designates gas-liquid chromatography.

EXAMPLE 1

Preparation of
N-4-(p-Chlorophenyl)-2-(trifluoromethyl)-5-oxazolylacetamide

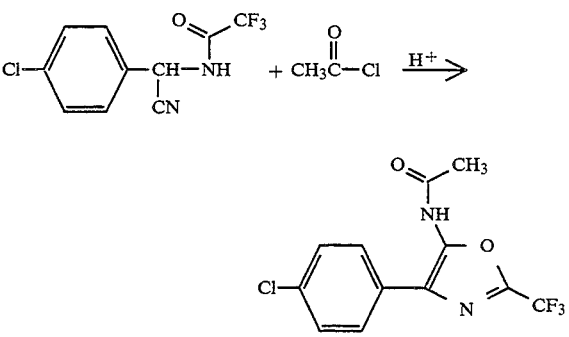

A slurry of N-[(p-chlorophenyl)cyanomethyl]-2,2,2-trifluoroacetamide (13.1 g, 0.05 mol) in toluene is treated with methanesulfonic acid (2.4 g, 0.025 mol) at room temperature. The reaction mixture is treated with acetyl chloride (4.32 g, 0.055 mol), heated at 80° C. for 2 hours, cooled and filtered. The filter cake is dissolved in ethyl acetate, washed with water and concentrated in vacuo to give a residue. The residue is crystallized from ethyl acetate/heptane to give the title product as a white solid, 13.8 g (90% yield), mp 207.5°–208.5° C., identified by IR, $^1$HNMR, $^{13}$CNMR and $^{19}$FNMR analyses.

EXAMPLE 2

Preparation of Ethyl N-4-(p-Chlorophenyl)-2-(trifluoromethyl)-5-oxazolyloxamate

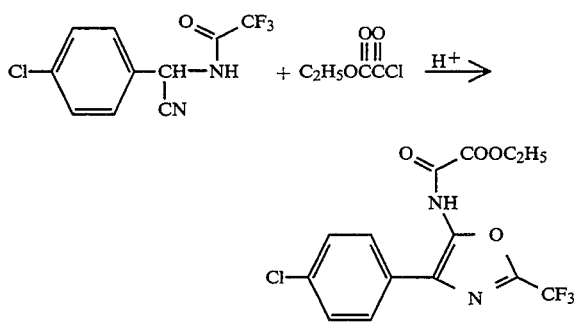

A stirred mixture of N-[(p-chlorophenyl)cyanomethyl]-2,2,2-trifluoroacetamide (39.4 g, 0.15 mol), methanesulfonic acid (14.4 g, 0.015 mol) and ethyl oxalyl chloride (22.5 g, 0.165 mol) in toluene is heated at 80° C. for 2 hours, cooled to room temperature and diluted with ethyl acetate. The reaction solution is washed with water and concentrated in vacuo to give a solid residue. The residue is recrystallized from toluene-heptane to give the title product as white crystals, 41.8 g (70% yield), mp 107.0°–108.5° C., identified by IR, $^1$HNMR, $^{13}$CNMR and $^{19}$FNMR analyses.

EXAMPLE 3

Preparation of 5-(Acylamino)-4-aryl-2-perfluoroalkyl-1,3-oxazole

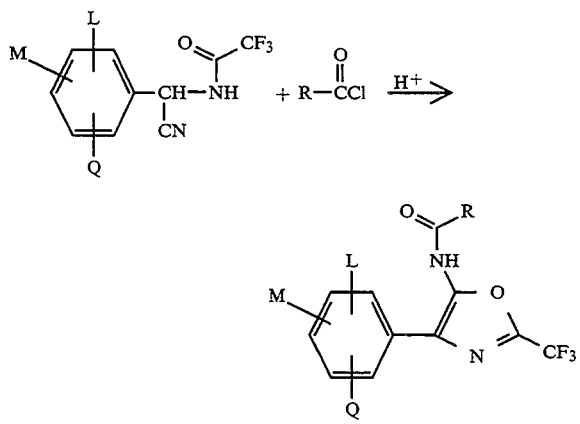

Using essentially the same procedures described in Examples 1 and 2 hereinabove the following acyamino oxazoles shown in Table I are obtained.

TABLE I

| L | M | Q | R | mp °C. |
|---|---|---|---|---|
| H | 4-CF$_3$ | H | —CH$_3$ | 187.0–187.5 |
| H | 4-Br | H | —CH$_3$ | 215.0–216.0 |
| 3-Cl | 4-Cl | H | —CH$_3$ | 171.0–172.0 |
| H | 4-Cl | H | —C$_6$H$_5$ | 172–176 |
| H | 4-CF$_3$ | H | —C$_6$H$_5$ | 146–149 |
| H | 4-Br | H | —C$_6$H$_5$ | 167–170 |
| 3-Cl | 4-Cl | H | —C$_6$H$_5$ | 180–182 |

EXAMPLE 4

Preparation of 2-(p-Chlorophenyl)-5-(trifluoromethyl)pyrrole-3-carbonitrile

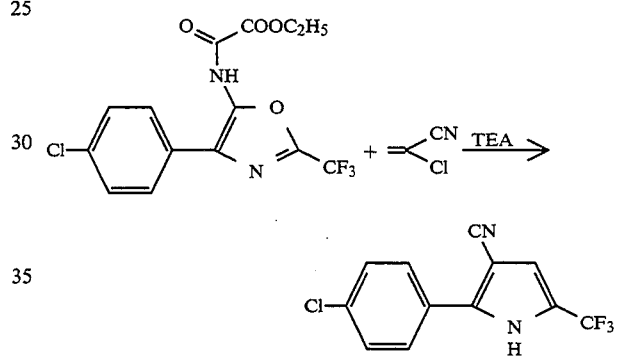

A solution of ethyl N-4-(p-chlorophenyl)-2-(trifluoro-methyl)-5-oxazolyloxamate (10.9 g, 0.03 mol) in acetonitrile is treated with 2-chloroacrylonitrile at room temperature. The reaction mixture is treated dropwise with triethylamine (TEA)(7.3 g, 0.072 mol), heated at 70°–72° C. for 5 hours, cooled to room temperature and diluted with water. The diluted reaction mixture is extracted with ethyl acetate. The extracts are combined, washed with water and concentrated in vacuo to give a semisolid residue. The residue is dissolved in 1:1 ethyl acetate:heptane and filtered through silica gel. The filtrate is concentrated in vacuo to give a solid residue. The solid is recrystallized from ethyl acetate-heptane to give the title product as a white solid, 4.6 g (57% yield), mp 238°–241° C., identified by $^1$HNMR, $^{19}$FNMR, GLC and HPLC analyses.

EXAMPLE 5

Preparation of 2-(p-Chlorophenyl)-5-(trifluoromethyl)pyrrole-3-carbonitrile

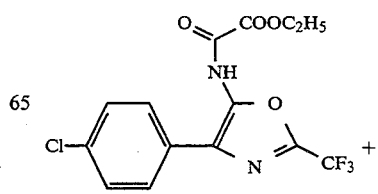

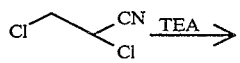
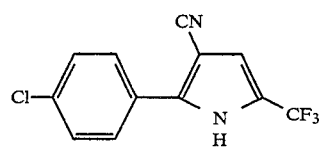

Using essentially the same procedure described above in Example 4 and substituting 2,3-dichloropropionitrile in place of 2-chloroacrylonitrile and employing 3.4 equivalents of triethylamine, the title product is obtained in 58% yield.

EXAMPLE 6

Preparation of 2-(p-Chlorophenyl)-5-(trifluoromethyl)pyrrole-3-carbonitrile

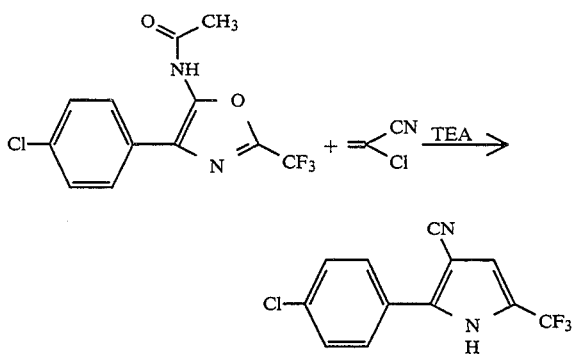

A slurry of N-4-(p-chlorophenyl)-2-(trifluoromethyl)-5-oxazolylacetamide (9.2 g, 0.03 mol) in acetonitrile is treated with 2-chloroacrylonitrile (3.15 g, 0.036 mol). The reaction mixture is treated dropwise with triethylamine (7.3 g, 0.072 mol), heated at 72°–75° C. for 2 hours, cooled to room temperature and diluted with water. The diluted mixture is extracted with ethyl acetate. The extracts are combined, washed with water and concentrated in vacuo to give a semi-solid residue. Flash chromatography of the residue (silica gel, 15% ethyl acetate in heptane eluent) gives the title product as a pale yellow solid, 3.7 g (46% yield), mp 238°–241° C., identified by $^1$HNMR and $^{19}$FNMR analyses.

EXAMPLE 7

Preparation of 2-(p-Chlorophenyl)-5-(trifluoromethyl)pyrrole-3-carbonitrile

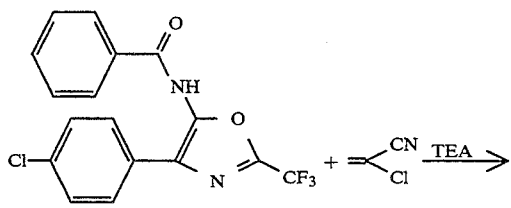

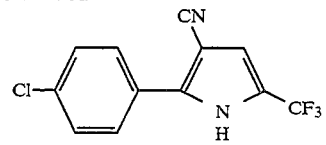

A slurry of N-4 (p-chlorophenyl)-2-(trifluoromethyl)-5-oxazolylbenzamide (14.7 g, 0.04 mol) in acetonitrile is treated with 2-chloroacrylonitrile (4.2 g, 0.048 mol). The reaction mixture is treated dropwise with triethylamine (9.72 g, 0.096 mol), heated at 70°–72° C. for 1 hour, cooled to room temperature and diluted with water. The diluted mixture is extracted with ethyl acetate. The extracts are combined, washed with water and concentrated in vacuo to give a waxy solid residue. Flash chromatography (silica-gel; 15% ethyl acetate in heptane as eluent) gives the title product as a pale yellow solid, 6.2 g (47% yield), mp 240°–242° C., identified by $^1$HNMR and $^{19}$FNMR analyses.

EXAMPLE 8

Preparation of 2-Aryl-5-perfluoroalkylpyrrole-3-carbonitrile

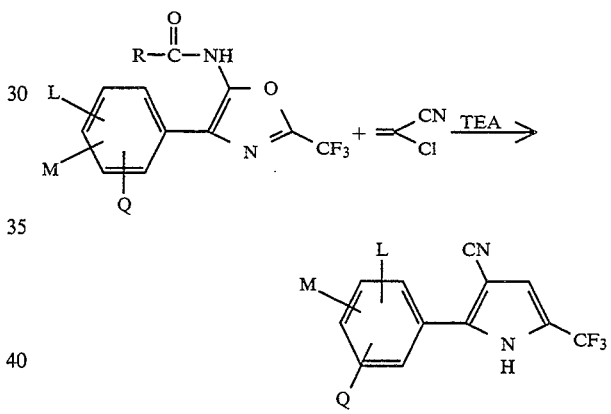

Using essentially the same procedures described in Examples 4–7 and employing the appropriate oxazole amine starting material, the following pyrrole compounds in Table II are obtained.

TABLE II

| Oxazole | | | | Pyrrole | |
|---|---|---|---|---|---|
| R | L | M | Q | mp °C. | % Yield |
| —CH$_3$ | H | 4-Br | H | >230 | 69 |

TABLE II-continued

| | | | | | |
|---|---|---|---|---|---|
| —CH₃ | H | 4-CF₃ | H | 219–220 | 58 |
| —CH₃ | 3-Cl | 4-Cl | H | >240 | 64 |
| —C₆H₅ | H | 4-Br | H | >230 | 28 |

EXAMPLE 9

Preparation of 2-(p-Chlorophenyl)-5-(trifluoromethyl)pyrrole-3-carbonitrile

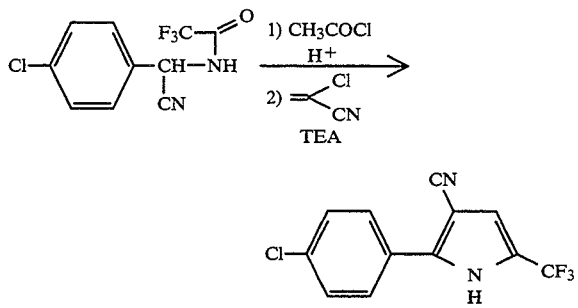

A slurry of N-[(p-chlorophenyl)cyanomethyl]-2,2,2-trifluoroacetamide (13.1 g, 0.05 mol) in toluene is treated sequentially with methanesulfonic acid (2.4 g, 0.025 mol) and acetyl chloride (4.32 g, 0.055 mol), at room temperature, heated at 80° C. for 2 hours, cooled to room temperature, diluted with acetonitrile, treated first with 2-chloroacrylonitrile (5.25 g, 0.06 mol) then dropwise with triethylamine (13.7 g, 0.135 mol), heated at 70°–72° C. for 1 hour, cooled to room temperature and diluted with water. The mixture is extracted with ethyl acetate. The extracts are combined, washed with water and concentrated in vacuo to give a residue. Flash chromatography (silica-gel; 15% ethylacetate in heptane as eluent) gives the title product.

I claim:

1. A process for the manufacture of an arylpyrrole compound of formula IV

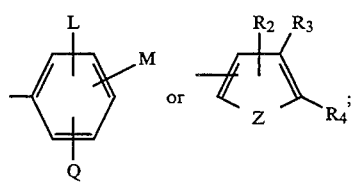 (IV)

wherein n is an integer of 1, 2, 3, 4, 5, 6, 7 or 8; and A is

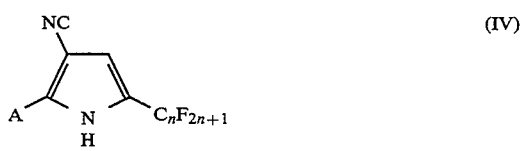

L is hydrogen or halogen;
M and Q are each independently hydrogen, halogen CN, NO₂, C₁-C₄alkyl, C₁-C₄haloalkyl, C₁-C₄alkoxy, C₁-C₄haloalkoxy, C₁-C₄alkylthio, C₁-C₄alkylsulfinyl or when M and Q are on adjacent positions they may be taken together with the carbon atoms to which they are attached to form a ring in which MQ represents the structure —OCH₂O—, —OCF₂O— or
—CH=CH—CH=CH—;

R₂, R₃ and R₄ are each independently hydrogen, halogen, NO₂, CHO or R₃ and R₄ may be taken together with the atoms to which they are attached to form a ring in which R₃R₄ is represented by the structure $$-\overset{R_5}{\underset{|}{C}}=\overset{R_6}{\underset{|}{C}}-\overset{R_7}{\underset{|}{C}}=\overset{R_8}{\underset{|}{C}}-;$$

R₅, R₆, R₇ and R₈ are each independently hydrogen, halogen, CN or NO₂; and
Z is O or S which comprises reacting an oxazole amine intermediate of formula I or tautomer thereof

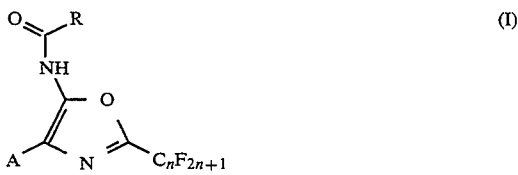 (I)

wherein n and A are described above and
R is C₁-C₆alkyl, C₁-C₆haloalkyl, COOR₁, or phenyl optionally substituted with one or more halogen, NO₂, CN, C₁-C₄alkoxy, C₁-C₄alkylthio, C₁-C₄alkyl or C₁-C₄haloalkyl groups;
R₁ is C₁-C₄alkyl or C₁-C₄haloalkyl with at least one molar equivalent of 2-haloacrylonitrile or 2,3-dihalopropionitrile in the presence of a base, optionally in the presence of a solvent.

2. The process according to claim 1 wherein the base is present in the amount of about one molar equivalent.

3. The process according to claim 1 wherein the base is an alkali metal carbonate, an alkali metal bicarbonate, an alkali metal hydroxide, an alkali metal acetate, tri(C₁-C₄alkyl)amine, 4-dimethylaminopyridine or pyridine.

4. The process according to claim 2 wherein the base is tri(C₁-C₄alkyl)amine.

5. The process according to claim 1 wherein R is C₁-C₄alkyl or phenyl.

6. The process according to claim 1 wherein A is

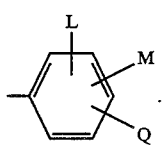

7. The process according to claim 1 wherein n is 1 or 2.

8. The process according to claim 1 wherein a solvent is present and the temperature is about 20°–100° C.

9. The process according to claim 8 wherein the solvent is acetonitrile or toluene, the base is triethylamine and the temperature is about 60°–90° C.

* * * * *